US006695834B2

(12) United States Patent
Gellman et al.

(10) Patent No.: US 6,695,834 B2
(45) Date of Patent: Feb. 24, 2004

(54) APPARATUS AND METHOD FOR STONE REMOVAL FROM A BODY

(75) Inventors: Barry N. Gellman, North Easton, MA (US); Jozef Slanda, Milford, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/057,147

(22) Filed: Jan. 25, 2002

(65) Prior Publication Data

US 2003/0144672 A1 Jul. 31, 2003

(51) Int. Cl.$^7$ .............................. A61B 17/22; A61N 5/06
(52) U.S. Cl. ..................... 606/2.5; 606/114; 606/128
(58) Field of Search ......................... 606/2.5, 47, 113, 606/114, 127, 128, 200, 108; 604/264; 623/1.11

(56) References Cited

U.S. PATENT DOCUMENTS

| | | | | |
|---|---|---|---|---|
| 4,590,938 A | * | 5/1986 | Segura et al. ............... 606/127 |
| 4,748,971 A | | 6/1988 | Borodulin et al. ......... 128/24 A |
| 4,823,773 A | | 4/1989 | Naser et al. .................. 128/24 |
| 4,823,793 A | * | 4/1989 | Angulo et al. ............... 606/128 |
| 4,905,691 A | * | 3/1990 | Rydell .......................... 606/47 |
| 4,927,427 A | * | 5/1990 | Kriauciunas et al. ........ 606/128 |
| 4,945,898 A | | 8/1990 | Pell et al. ...................... 128/24 |
| 5,065,761 A | | 11/1991 | Pell ......................... 128/660.03 |
| 5,129,910 A | | 7/1992 | Phan et al. .................. 606/127 |
| 5,176,688 A | * | 1/1993 | Narayan et al. ............. 606/128 |
| 5,192,286 A | | 3/1993 | Phan et al. .................. 606/127 |
| 5,311,858 A | | 5/1994 | Adair ............................ 128/4 |
| 5,357,805 A | | 10/1994 | Fujimoto et al. ............. 73/715 |
| 5,484,384 A | | 1/1996 | Fearnot .......................... 600/3 |
| 5,534,007 A | * | 7/1996 | St. Germain et al. ....... 623/1.11 |
| 5,693,069 A | | 12/1997 | Shallman ..................... 606/205 |
| 5,722,980 A | | 3/1998 | Schulz et al. ................ 606/128 |
| 5,788,710 A | * | 8/1998 | Bates et al. .................. 606/127 |
| 5,843,028 A | | 12/1998 | Weaver et al. ................. 604/54 |
| 5,868,756 A | | 2/1999 | Henry et al. ................. 606/128 |
| 5,906,622 A | | 5/1999 | Lippitt et al. ................ 606/127 |
| 5,951,570 A | | 9/1999 | Leibersperger et al. ..... 606/128 |
| 5,957,932 A | | 9/1999 | Bates et al. .................. 606/127 |
| 5,984,920 A | * | 11/1999 | Steinbach ..................... 606/47 |
| 6,096,053 A | | 8/2000 | Bates ........................... 606/159 |
| 6,099,534 A | | 8/2000 | Bates et al. .................. 606/127 |
| 6,159,220 A | | 12/2000 | Gobron et al. .............. 606/127 |
| 6,174,318 B1 | | 1/2001 | Bates et al. .................. 606/127 |
| 6,217,589 B1 | | 4/2001 | McAlister .................... 606/128 |
| 6,224,612 B1 | | 5/2001 | Bates et al. .................. 606/114 |
| 6,248,113 B1 | * | 6/2001 | Fina ............................ 606/127 |
| 6,264,664 B1 | * | 7/2001 | Avellanet .................... 606/128 |
| 6,319,261 B1 | * | 11/2001 | Bowers ....................... 606/127 |

FOREIGN PATENT DOCUMENTS

| | | | |
|---|---|---|---|
| DE | 33 40 581 | 6/1985 | |
| EP | 0 467 501 A1 | 1/1992 | |
| WO | WO 99/17669 | 4/1999 | |
| WO | 99/53850 | 10/1999 | ............. 17/22 |

OTHER PUBLICATIONS

International Search Report for International Application No. PCT/US03/00261 mailed May 2, 2003.

* cited by examiner

*Primary Examiner*—Michael J. Milano
*Assistant Examiner*—D. Jacob Davis
(74) *Attorney, Agent, or Firm*—Testa, Hurwitz & Thibeault LLP

(57) ABSTRACT

A device for treating material in a body of a patient includes an expandable basket having a projection for securing material within the basket. The projection has a distal end joined to a distal tip of the basket and a proximal end extending within a lumen of the basket.

20 Claims, 14 Drawing Sheets

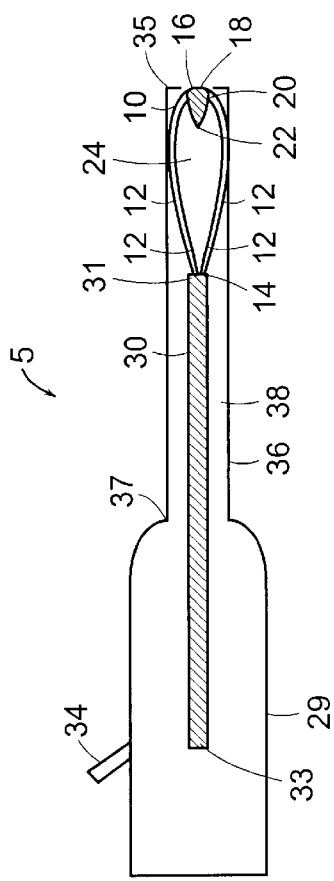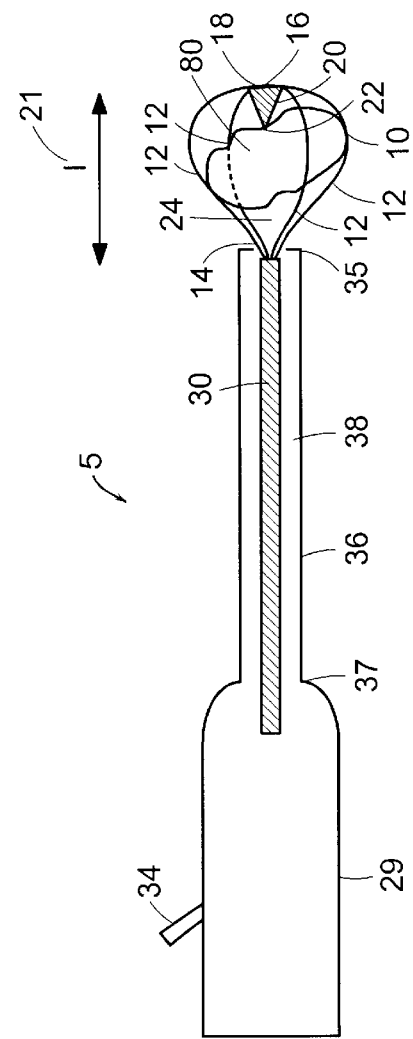

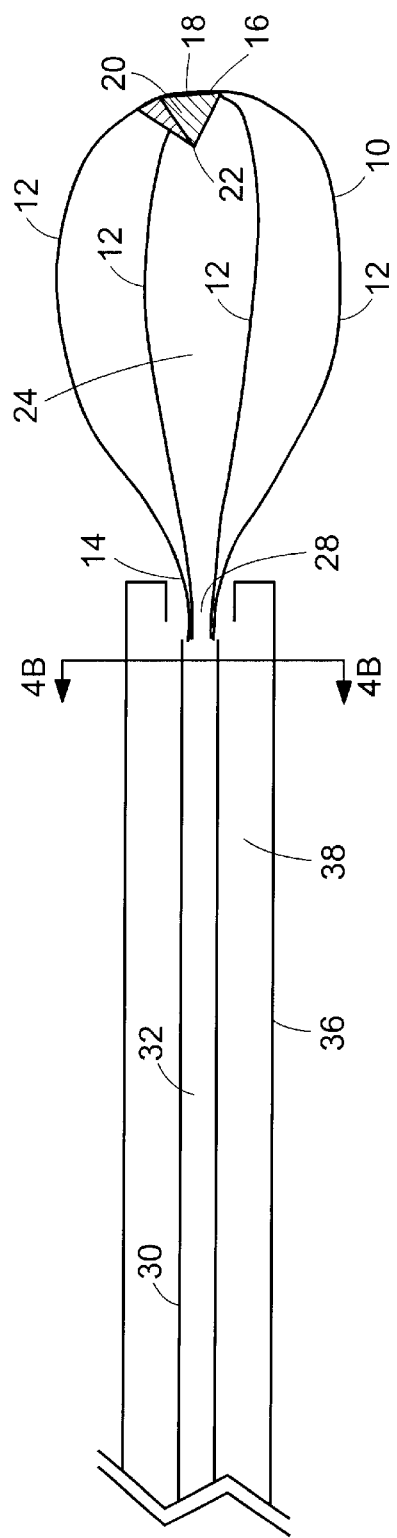
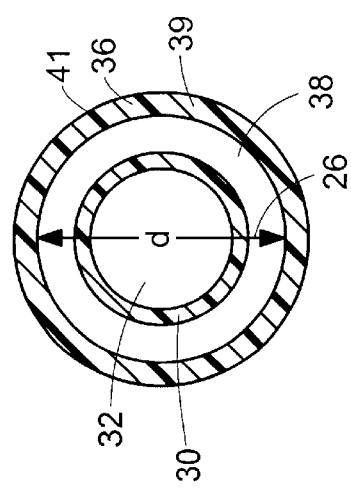
FIG. 4A
FIG. 4B

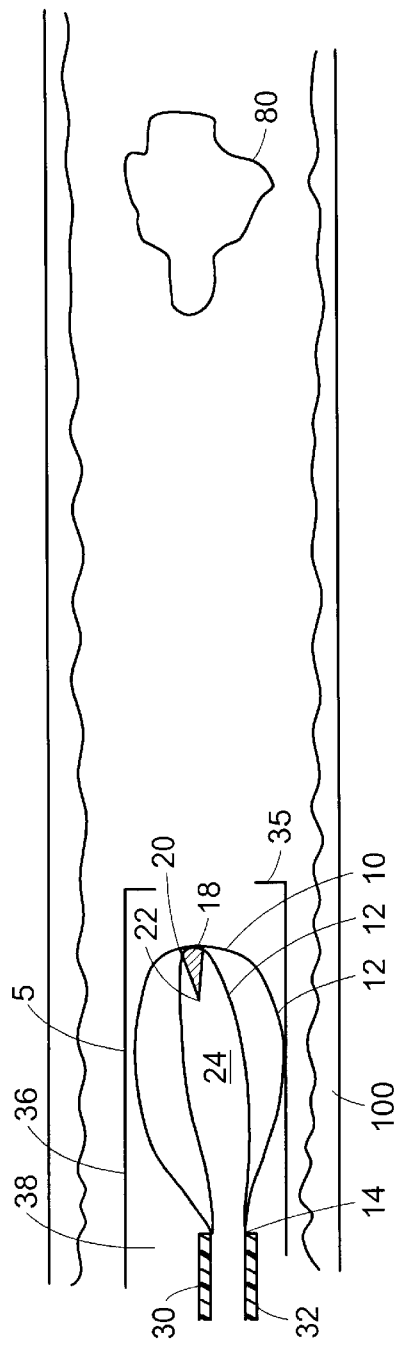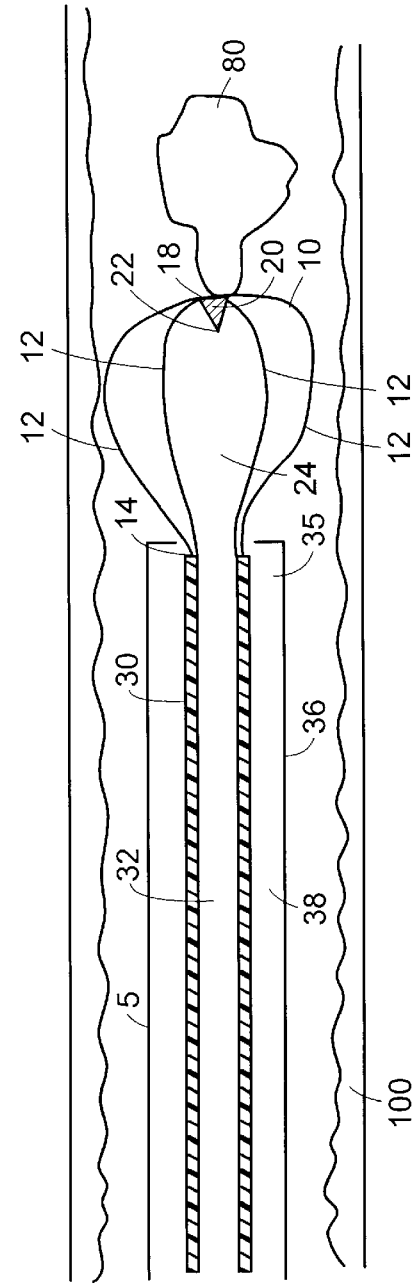

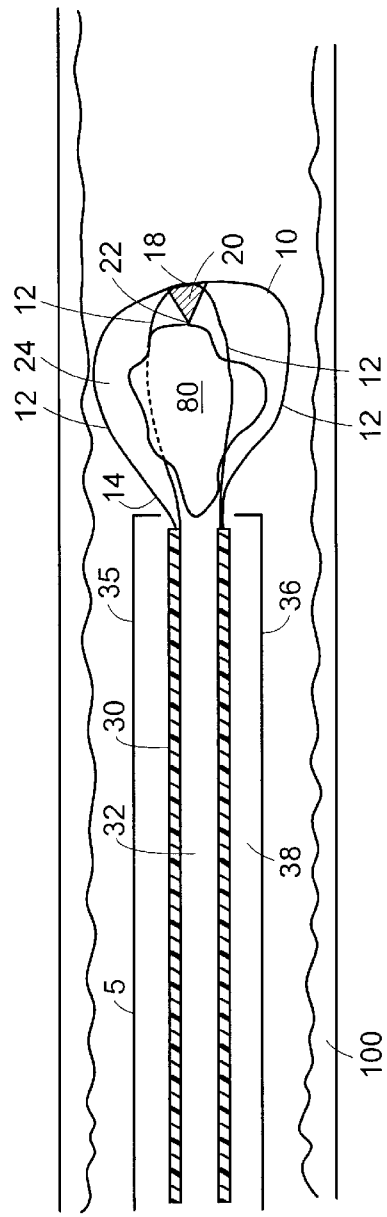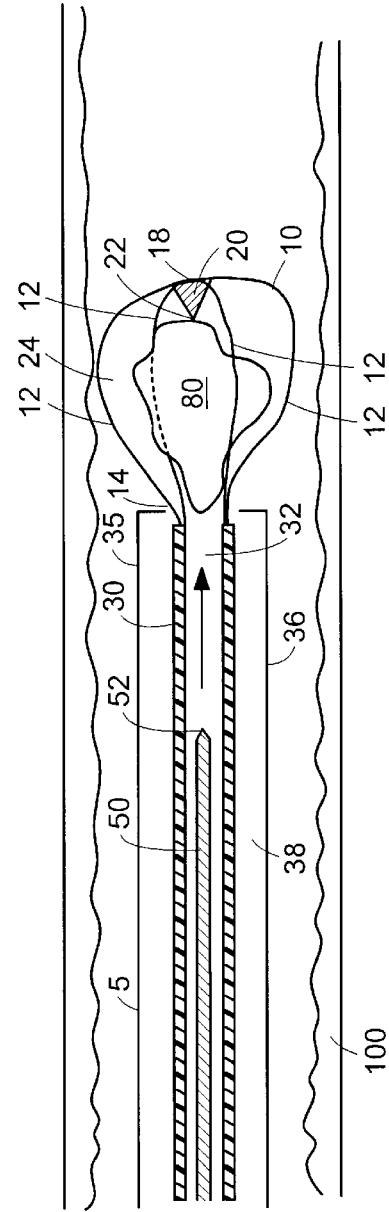

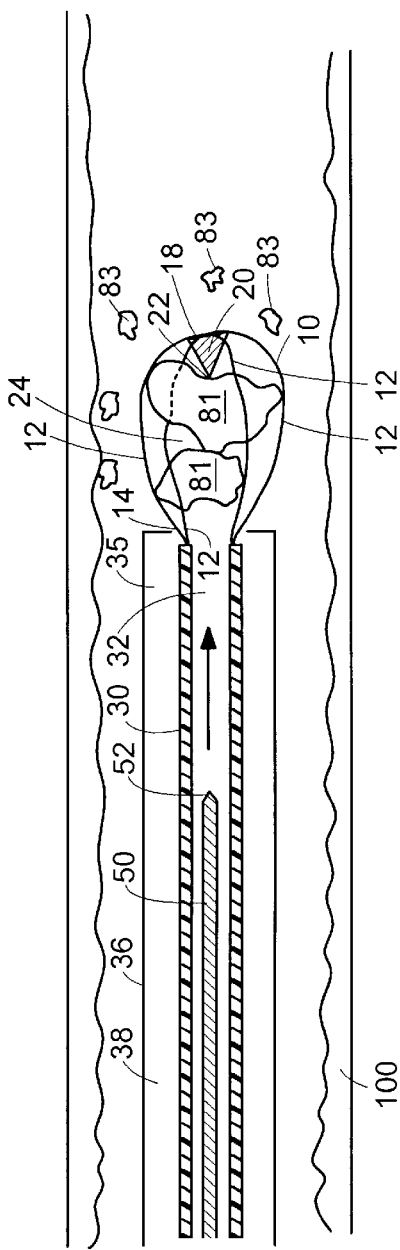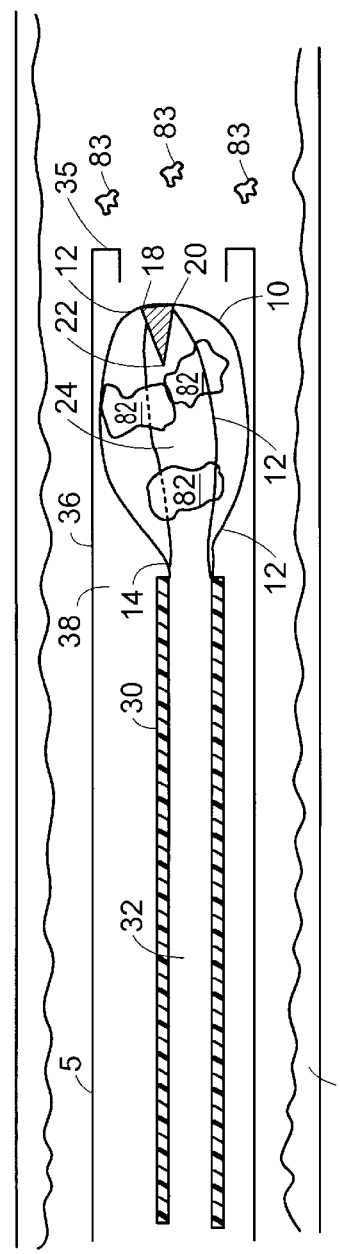
FIG. 8E
FIG. 8F

APPARATUS AND METHOD FOR STONE REMOVAL FROM A BODY

TECHNICAL FIELD

The invention generally relates to medical devices for retrieving material from within a body. More particularly, the invention relates to medical retrieval baskets that have a projection proximally extending from a distal tip of the basket to enhance the basket's ability to secure or fragment material (e.g., stones) captured from a body lumen.

BACKGROUND INFORMATION

Medical baskets are used to retrieve biological material from a body. For example, medical baskets are commonly used to retrieve stones from a patient's urinary tract or biliary tree. Medical baskets may or may not be used through a catheter, an endoscope, or a laparoscope.

Existing medical baskets generally have two or more legs, which are joined together to form the basket. The number, flexibility, shape, and length of the legs defines an overall shape of a particular medical basket. At a proximal base of the basket, the joined legs typically are attached to an elongated member, such as, for example, a shaft, wire, or coil. The elongated member can be moved back and forth within a sheath or catheter by an actuation device, such as, for example, a back-and-forth hand-activated slider located on the proximal end of the sheath. Alternatively, the sheath can move back and forth to expose and cover the basket. In any case, the basket is fully expanded when exposed, fully collapsed when covered by the sheath, or somewhere in between these two extremes.

To retrieve a stone or other biological material from the patient's body, a medical professional, such as a physician, inserts a device including the medical basket into the patient's body, locates the stone, captures the stone within the basket by first expanding the basket and then collapsing the basket around the stone. Finally the medical professional removes the device with captured stone from the patient's body. In some cases, the medical professional may desire to crush or break the stone into smaller pieces in situ prior to removal to facilitate natural passage of the stone or to facilitate removal of the stone within the basket. In these cases, a procedure known as lithotripsy can be performed through a catheter device attached to the basket.

SUMMARY OF THE INVENTION

It is an object of the invention to provide a medical instrument for treating material in a patient's body. The medical instrument includes a basket having a plurality of basket legs and a projection extending from the distal end of the basket proximally into a basket lumen. The plurality of basket legs and the projection secures material captured within the basket lumen and inhibits material from escaping from the medical instrument. The projection may also assist in breaking apart material captured within the basket lumen.

It is another object of the invention to provide a medical instrument that allows material to be captured, fragmented, and retrieved from a patient's body. The medical instrument further includes a lithotriptor that can access material captured within the basket.

It is yet another objection of the invention to provide a method of using such baskets to retrieve material from within a body. The material can be, for example, urological stones or any variety of other types of material found in the body.

A device for treating material in a body according to one aspect of the invention includes a sheath and an expandable basket. The sheath includes a sheath wall, a distal end, a proximal end, and a lumen extending within the sheath. The expandable basket is slidably receivable by the lumen of the sheath and has a collapsed position where the basket is enclosed within the sheath and an expanded position where the basket extends from the distal end of the sheath. The basket includes a distal tip, a proximal end, a lumen, and a projection. The projection has a distal end joined to the distal tip of the basket and a proximal end that is free within the lumen of the basket.

In accordance with one aspect of the invention, the device may include a projection having at least one tip. The tip may be sharp to facilitate breakage of the material captured within the basket. The device may further include the following features. The device may have an elongated member axially positioned within the lumen of the sheath and operatively joined to the proximal end of the basket. The elongated member may include a lumen extending therethrough and in fluid communication with the basket lumen to allow the passage of a lithotriptor or liquids to pass through the elongated member to the basket lumen. In one embodiment, a basket handle for controlling the position of the basket may be positioned at the proximal end of the sheath. The handle may include a spring operatively joined to the elongated member. The spring provides a predetermined force on the basket to withdraw the basket legs into the sheath upon the handle's release. In an alternative embodiment, the handle may include a slider to move the sheath axially from a first position to a second position to expose and cover the basket. The device may further include a reinforced distal end to prevent damage to the sheath during movement of the sheath from the first position to the second position.

The device may also include a lithotriptor for fragmenting material captured within the basket. In one embodiment the lithotriptor includes an energy source, an actuator, and a return spring. In an alternative embodiment, the lithotriptor includes an optical cable and a laser. In another embodiment, the device may include a wire for deflecting the sheath. The wire includes a distal portion, an intermediate portion, and a proximal portion. The distal portion of the wire is attached to the distal end of the sheath. In some embodiments, the wire extends along an external surface of the sheath, the intermediate portion of the wire penetrates the sheath wall, and the proximal portion extends proximally within the lumen of the sheath. In an embodiment of the device including the wire for deflection of the sheath, the device may include an elongated member including a distal portion and a proximal portion. The distal portion of the elongated member includes an elastic material, such as, a shape memory alloy or a spring that can be deflected with the sheath and then return to its original shape.

Another aspect of the invention relates to a method for retrieving material from a body including the steps of inserting a device including a basket with a projection, such as the baskets described above into a patient's body, placing the basket in an expanded position, maneuvering the basket to grasp the material, collapsing the basket around the material, and withdrawing the device from the body to remove the grasped material from the body.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead being placed upon illustrating the principles of the invention.

FIG. 1A is a plan view of an embodiment of a device for retrieving material from a body in a collapsed position.

FIG. 2A is a plan view of the device illustrated in FIG. 1A in an expanded position.

FIG. 4A is a plan view of a portion of an embodiment of the device of the invention.

FIG. 4B is a cross-sectional view of the device of the invention taken along line A—A of FIG. 4A.

FIGS. 8A–8F are diagrammatic representations of a clinical application of one embodiment of the device illustrated in FIG. 6.

DESCRIPTION

The invention described herein is a medical instrument for treatment of material in a body. The medical instrument has a basket, which may be used for capturing, manipulating or removal of the material. The following embodiments of the invention have at least one feature in common, a projection extending from a distal end of a basket proximally into a basket lumen.

Figure 1B:
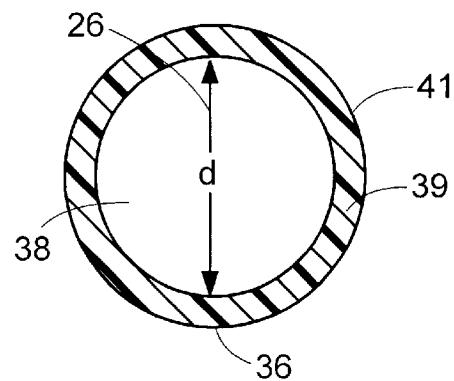
FIG. 1B is a cross-sectional view of one embodiment of a sheath of the invention.
Figure 1C:
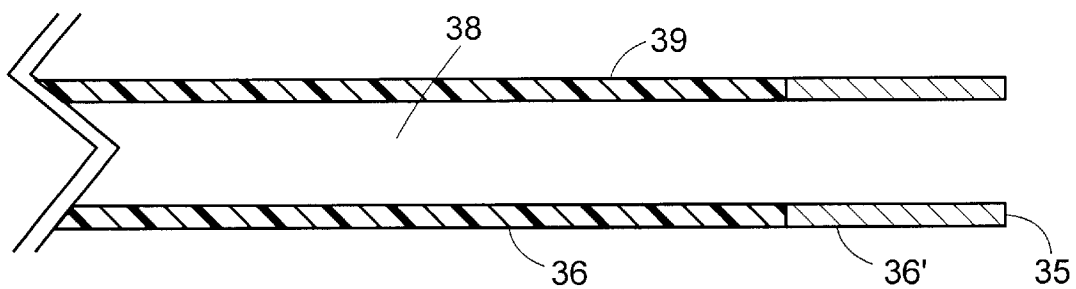
FIG. 1C is a longitudinal cross-sectional view of another embodiment of the sheath having a reinforced distal end portion.

FIG. 1A illustrates a device 5 for treating material in a body according to the present invention. In the embodiment shown in FIG. 1A, the device 5 includes a basket 10 and a sheath 36. The basket 10 is the type that can be collapsed within the sheath 36. The basket 10 and the sheath 36 are not shown in their correct size or proportion to each other. Typically, the sheath 36 is much longer than the basket 10 to allow insertion into a patient's body cavity, canal, or tract. The size of the sheath 36 is dimensioned to fit the requirements of its application in the body. For example, for urological applications, the size of the device is typically 1.7 to 8.0 Fr. The sheath 36 is typically made from a biocompatible material and includes a distal end 35, a proximal end 37, and at least one lumen 38. The lumen 38 of the sheath 36 has an internal diameter "d" 26 and is defined by a sheath wall 39, as illustrated in FIG. 1B. The sheath wall 39 has an external surface 41. In some embodiments, such as the embodiment shown in FIG. 1C, a portion 36' of the sheath 36 adjacent to the distal end 35 may be reinforced with a rigid material to prevent damage to the sheath 36 and to facilitate collapse of the basket 10 during use. The portion 36' of the sheath 36 may be in the range of 0.05 inches to the entire length of the sheath 36. Preferably, the portion 36' has a length of 0.10 inches. The length of the sheath 36 may be 12 to 36 inches, preferably 15 inches.

In the embodiment shown in FIG. 1A, the device 5 further includes an elongated member 30, such as, for example, a shaft, catheter, cable, coil, or guidewire, and a handle 29 attached to the proximal end 37 of the sheath 36. The elongated member 30 extends within the lumen 38 of the sheath 36 and has a distal end 31 joined to the proximal end 14 of the basket 10 and a proximal end 33. The handle 29 contains an actuating mechanism 34, which is operatively joined to the sheath 36. Operation of the actuating mechanism 34 by an operator causes the sheath 36 to either advance over the stationary basket 10, thereby collapsing the basket 10 within the sheath 36, as illustrated in FIG. 1A, or causes the sheath 36 to retract, thereby exposing the basket 10 and allowing the basket 10 to expand beyond the distal end 35 of the sheath 36, as illustrated in FIG. 2A. Alternatively, the actuating mechanism 34 can be operatively joined to the elongated member 30 and movement of the actuating mechanism 34 can cause the basket 10 to move in and out of the sheath 36 between a collapsed position within the sheath 36 and an expanded position outside of the sheath 36.

With continued reference to FIGS. 1A and 2A, the basket 10 has a plurality of legs 12. The basket legs 12 define an outer shape of the basket 10. The basket legs 12 may be made from a resilient material, such as, metal wires that can be easily deflected under a compressive force and subsequently return to their original configuration in the absence of the compressive force. The basket 10 may be collapsed, as shown in FIG. 1A, when located completely within a lumen 38 of the sheath 36, expanded, as shown in FIG. 2A, when located beyond a distal end 35 of the sheath 36, or somewhere in between collapsed and expanded.

Still referring to FIGS. 1A and 2A, the basket 10 also includes a distal tip 16 positioned at the distal end of the device 5, a proximal end 14 proximal to the distal tip 16 and distal to the elongated member 30, a basket lumen 24, and a projection 20. The projection 20 may be formed from a resilient, rigid material, such as, for example, stainless steel, titanium, or nickel and has a distal end 18 and a proximal end 22. Projection 20 is attached to the basket 10 such that the distal end 18 of the projection is joined to the luminal side of the distal tip 16 of the basket 10 by, for example, selective welding, adhesive, or thermal bonding. The proximal end 22 of the projection 20 projects into and is free within the lumen 24 of the basket 10. The projection 20 projects into the lumen 24 of the basket 10 in a range of about 1% to 35%, preferably 10% of basket length "1" indicated by line 21 in FIG. 2A when the basket 10 is in an expanded position.

Material 80 captured within the lumen 24 of the basket 10 is held in the lumen 24 by the projection 20 and legs 12. The projection 20 may also serve to facilitate breakage of material 80 captured within the lumen 24. Projection 20 of the basket 10 assists in holding material 80 within the lumen 24 of the basket 10 and assists in breaking the material 80 apart.

Figure 2B:
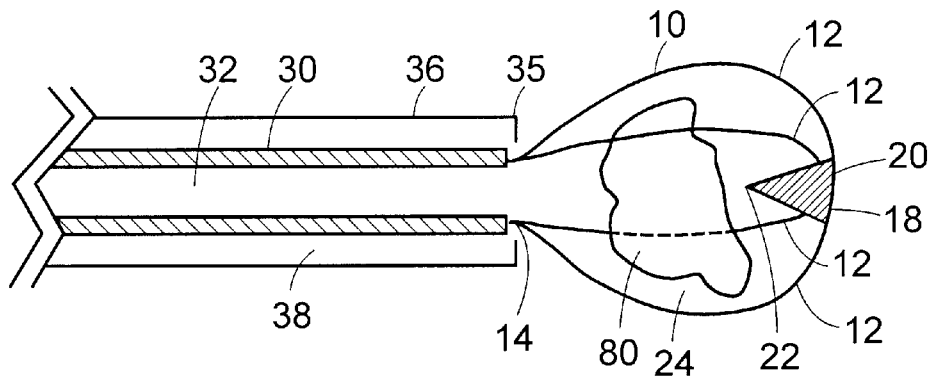
FIG. 2B is a schematic view of one embodiment of a portion of the device with captured material within a basket of the invention.
Figure 2C:
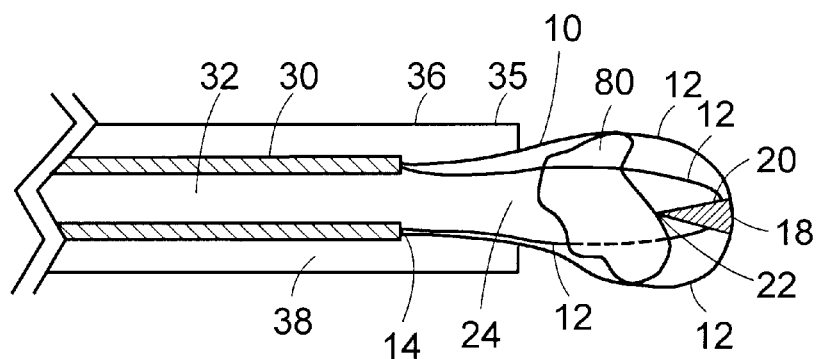
FIG. 2C is a schematic view of the portion of the device illustrated in FIG. 2B after fragmentation of the material.

For example, as illustrated in FIGS. 2B and 2C, the proximal end 22 of projection 20 provides at least one counter pressure point to aid in breaking the material 80 apart in the lumen 24 of the basket 10. In one instance, the material 80 in the lumen 24 of the basket 10 may be broken apart by advancing the sheath 36 over the basket 10 in the expanded position, thereby collapsing the basket 10 around the material 80 and advancing the material 80, such as a stone 80, against the proximal end 22 of the rigid projection 20. Further collapse of the basket 10 as the sheath 36 is moved over the basket 10, further advances the material 80 distally against the projection 20, causing the material 80 to fracture, then break apart.

Alternatively, the sheath 36 may remain in a stationary position and the elongated member 30, attached by its distal end 31 to the proximal end 14 of the basket 10, is withdrawn proximally by the actuating member 34 on handle 29. The basket 10 moves from the expanded position illustrated in FIG. 2A towards the collapsed position illustrated in FIG. 1A, thereby advancing the material distally in the lumen 24 of the basket 10 against the proximal end 22 of the projection 20. Further withdrawal of the elongated member 30 forces the material 80 against projection 20 causing the material to fracture and break apart.

FIGS. 1A and 2A show one embodiment of the projection 20. Alternative projection embodiments are possible so long as these embodiments inhibit distal movement of material captured within the lumen 24 and also provide a surface to facilitate breakage of material. Some other possible projection embodiments are shown in FIGS. 3A–E.

Figure 3A:
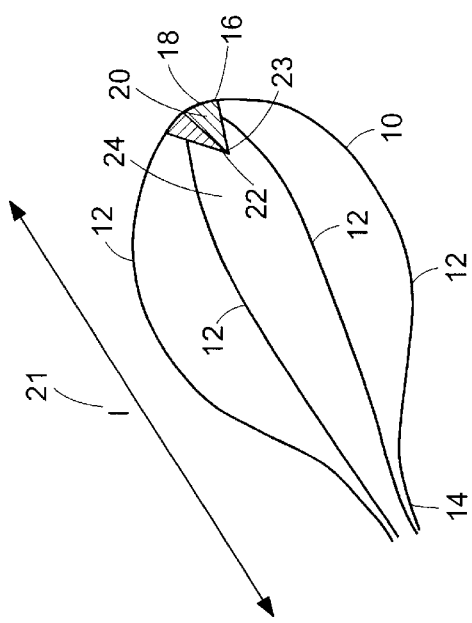
FIG. 3A is a schematic view of one embodiment of a basket of the invention comprising a projection including a single sharp tip at its proximal end.
Figure 3C:
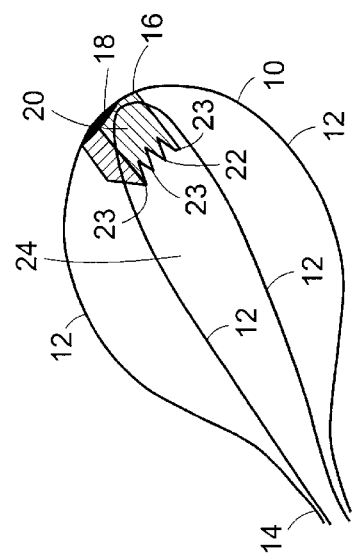
FIG. 3C is a schematic view of another embodiment of the basket comprising a projection including a plurality of sharp tips at its proximal end.
Figure 3B:
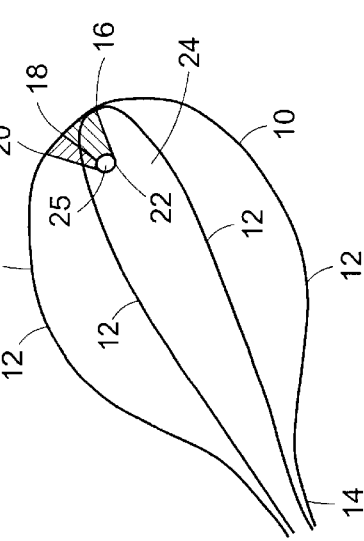
FIG. 3B is a schematic view of another embodiment of the basking comprising a projection including a single blunt tip at its proximal end.

For example, FIG. 3A shows a pyramidal embodiment of the projection 20. According to the embodiment shown in FIG. 3A, the pyramidal projection 20 has a single sharp tip 23 at its proximal end 22 and at least 3 sides. Generally, the sharp tip 23 at the proximal end 22 of the projection 20 will introduce a crack on the surface of material 80 collected within the basket 10 upon contact of the material 80 with the projection 20. The crack introduced on the surface of the material 80 will facilitate breakage of the material 80 within the basket 10. In an alternative embodiment illustrated in FIG. 3B, the projection 20 has a blunt tip 25 at the proximal end 22 of the projection 20. The blunt tip 25, typically, provides the proximal end 22 with increased surface area as compared to the single sharp tip 23 as illustrated in FIG. 3A and provides the basket 10 with increased material 80 retention capabilities. In yet another embodiment illustrated in FIG. 3C, the projection 20 includes a plurality of sharp tips 23 at the proximal end 22 of the projection 20. This embodiment provides the advantage of introducing multiple crack initiation sites on the surface of the material 80 upon contact of the projection 20 with the material 80 captured within the basket 10. Additionally, the projection 20, as shown in FIG. 3C, has a greater surface area as compared to the embodiment of projection 20 shown in FIG. 3A, in which to retain captured material 80 within the basket 10.

Figure 3E:
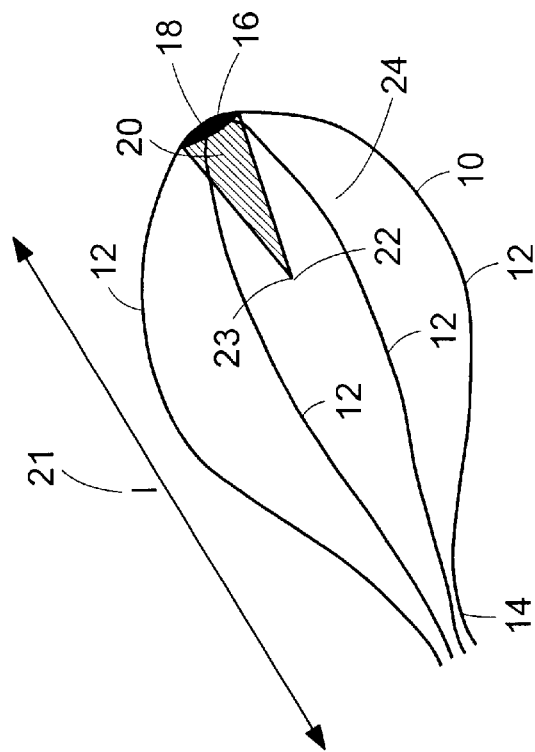
FIG. 3E is a schematic view of another embodiment of the basket comprising a projection having a greater distance between its distal and proximal ends than the projection illustrated in FIG. 3D.
Figure 3D:
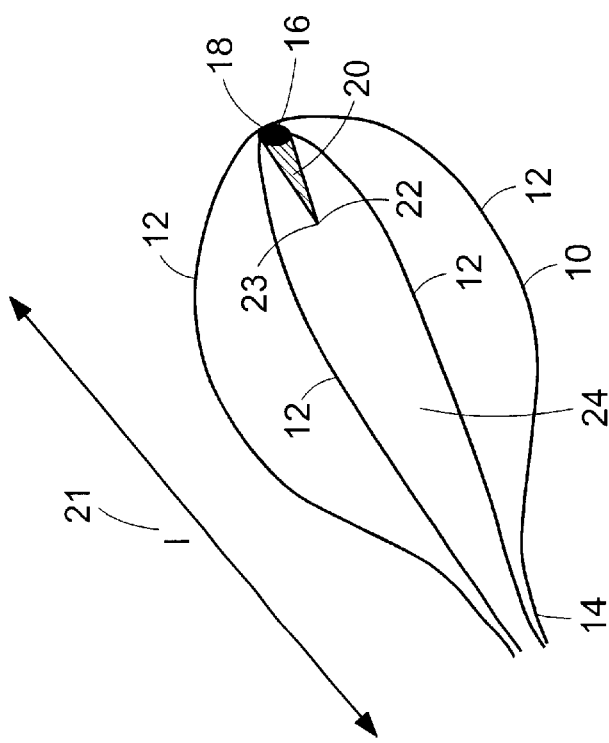
FIG. 3D is a schematic view of another embodiment of the basket comprising a projection having a short distance between its distal and proximal ends.

In yet another embodiment according to the invention, FIGS. 3D and 3E show conical shaped projections 20. The projections 20 shown in these embodiments have a single sharp tip 23 for inducing crack formation on the surface of material captured within the basket 10. The projection 20 shown in FIG. 3D has a shorter distance between its proximal end 22 and distal end 18 as compared to the embodiment shown in FIG. 3E. The length of projection 20 illustrated in FIG. 3D spans 5% of the basket length "1" 21, whereas the projection 20 in FIG. 3E spans 30% of the basket length 21. Projections 20 with a large distance between the distal end 18 of projection 20 and proximal end 22 may be desirable when capturing material having a dimension substantially smaller than the length 21 of the basket 10. A long projection 20 may enhance an operator's ability to capture and retain material 80 of a small size between the proximal end 22 of the projection 20 and the proximal end 14 of the basket 10, because by having a long projection 20, the distance the proximal end 14 of the basket 10 must travel to ensnare the material 80 is minimized, thereby presenting little opportunity for the material 80 to escape from the lumen 24 of the basket 10.

Referring to FIGS. 4A–4B, in one embodiment, the elongated member 30 may include a lumen 32 extending longitudinally therethrough. The lumen 32 in the elongated member 30 is in fluid communication with the lumen 24 of the basket 10. The lumen 32 thereby provides an access port 28 to the basket 10 when the device 5 is inserted into the body of the patient. FIG. 4B shows a cross-sectional view of the sheath 36 and the elongated member 30 located within. The lumen 38 of the sheath 36 is defined by the sheath wall 39. The elongated member 30 lies within the lumen 38 of the sheath 36 and the lumen 32 extends within the elongated member 30. In some embodiments, the lumen 32 may be sized to accommodate a lithotriptor 50 as shown in FIG. 5 or may serve as a conduit to the lumen 24 of the basket 10 for liquids, such as drugs.

Figure 5:
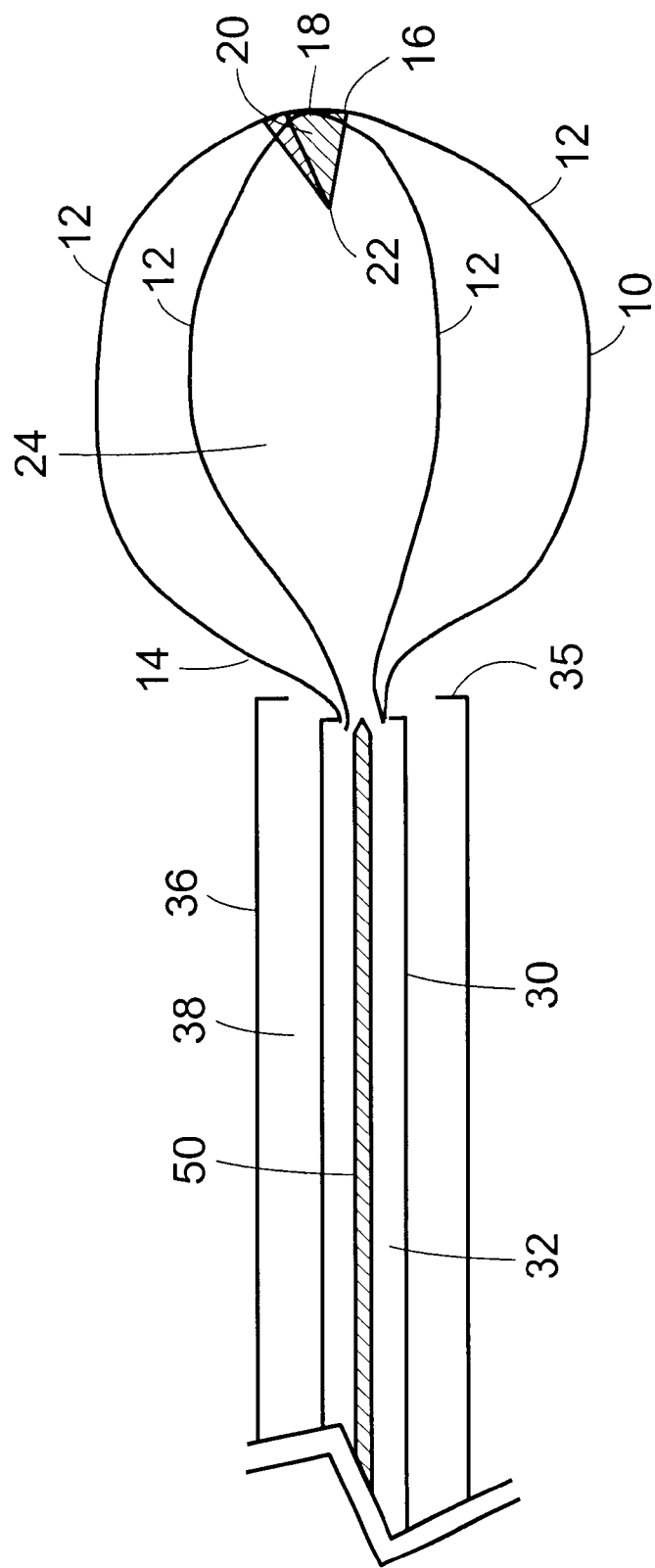
FIG. 5 is a plan view of a portion of the device of the invention with a lithotriptor located within a lumen of an elongated member.

FIG. 5 illustrates yet another embodiment of the present invention. The device 5 further includes a lithotripsy system for breaking the material 80 captured within the basket 10 in situ prior to removal of the device 5 from the body. FIG. 5 shows a side view of a distal portion of the device 5 with a lithotriptor 50. The lithotriptor 50 is slidably moveable within the lumen 32 of the elongated member 30. The lithotriptor 50, when activated supplies a force to break, apart material 80 captured within the basket 10. In one embodiment according to the invention, the lithotriptor 50, illustrated in FIG. 5 is a metal rod 50 that is forced, for example, pneumatically, (energy source) into the lumen 24 of the basket 10 to impact the material captured within the lumen 24. To control the release of the metal rod 50, an operator activates an actuator. The metal rod 50 may be attached within the device 5 by a return spring to return the metal rod 50 to its original position within the device after being forced through the lumen towards the material 80 captured in the basket 10. In another embodiment, the lithotriptor 50 may be a fiber optic cable in optical communication with a laser. In this embodiment, not shown, a laser beam is transported through the device 5 via a fiber optic cable positioned in the lumen 32 of the elongated member 30 and is directed to the material 80, thereby transferring energy from the laser to the material 80 to fracture the material 80 within the basket 10. The material 80 is held in place by projection 20 while the material 80 is being fragmented. The lithotriptor 50 may be activated several times until the material 80 has broken apart sufficiently to facilitate passage of the material 80 through and out of the patient's body or to facilitate removal of the material 80 by the basket 10 from the patient's body.

Figure 6:
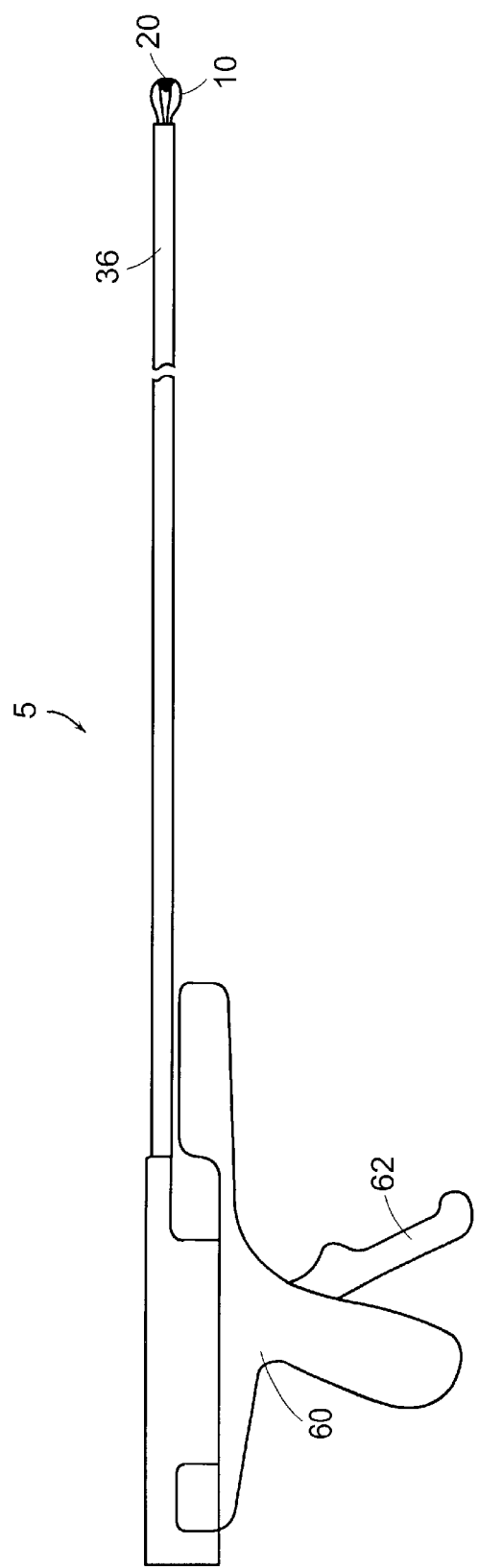
FIG. 6 is a plan view of another embodiment of the device for retrieving material from the body.
Figure 7A:
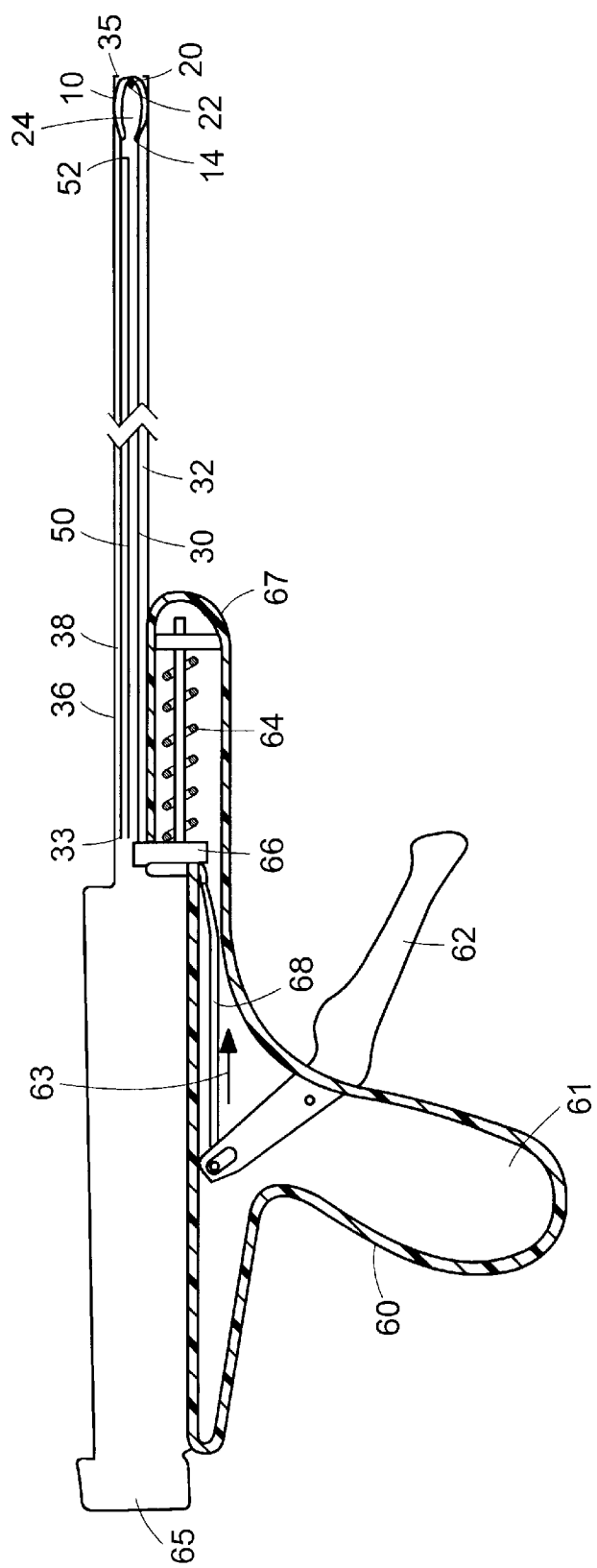
FIG. 7A is a cross-sectional view of one embodiment of the device in a collapsed position.
Figure 7B:
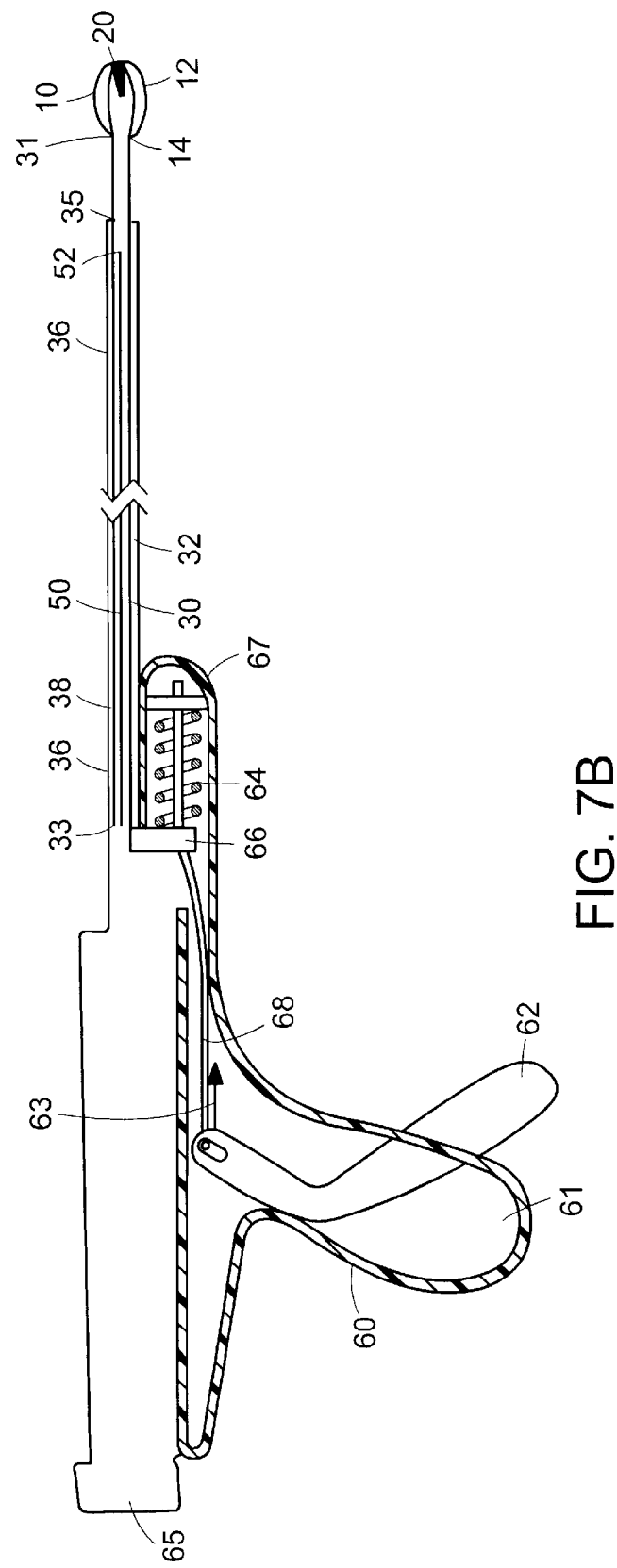
FIG. 7B is a cross-section view of the device illustrated in FIG. 7A in an expanded position.

In another embodiment according to the invention illustrated in FIG. 6, the handle 60 includes a trigger mechanism 62 for pushing the basket 10 out of the lumen 38 of the sheath 36. As shown in FIGS. 7A and 7B, the trigger mechanism 62 is operatively joined by a rod 68 to a spring 64 and to the elongated member 30, via transverse member 66. As the trigger mechanism 62 is displaced proximally toward grip 61 by an operator, rod 68 is advanced distally in the direction of arrow 63 thereby compressing spring 64 as illustrated in FIG. 7B. As spring 64 is compressed, the proximal end 33 of the elongated member 30 operatively joined to transverse member 66 is extended distally beyond the distal end 35 of the sheath 36. When the trigger mechanism 62 is released by the operator, the spring 64 returns to its relaxed, non-compressed position as shown in FIG. 7A, transverse member 66 moves proximally drawing the proximal end 33 of the elongated member 30 back into the sheath 36.

The spring 64 provides a predetermined force on the basket 10, thereby forcing the basket legs 12 to be withdrawn into the lumen 38 of the sheath 36 as illustrated in FIG. 7A upon release of the trigger mechanism 62. If the material 80 captured within the lumen 24 has a dimension greater than the internal diameter 26 of the sheath 36, the basket legs 12 are withdrawn partially into the lumen 38 of the sheath 36 and the basket 10 will partially collapse around the material 80. The material 80 within the partially collapsed basket 10 is secured within the lumen 24 of the basket 10 between the proximal end 22 of the projection 20, and the proximal end 14 of the collapsed or partially collapsed basket 10.

In another aspect, the device 5, according to the invention may be used for capturing and fragmenting material 80 in a body. FIGS. 8A–8F illustrate the steps of one embodiment of the method according to the invention for a clinical application. FIG. 8A shows a stone 80, such as a kidney or gall stone, located in a body tract 100. An operator, such as a physician, preferably under endoscopic guidance, advances the device 5 with the basket 10 retracted or in a collapsed position inside the lumen 38 of the sheath 36 until the distal end 35 of the device 5 is adjacent to the stone 80. Once the distal end 35 of the device 5 is positioned adjacent the stone 80, the operator activates the trigger mechanism 62 in the handle 60, corresponding to the handle illustrated in FIG. 7A, to transition the basket 10 from a collapsed position illustrated in FIG. 8A to an expanded position, shown in FIG. 8B. With the basket 10 in the expanded position, the operator maneuvers the basket 10 around the stone 80 to capture the stone 80 within the lumen 24 of the basket 10. Referring now to FIG. 8C, after capturing the stone 80 within the basket 10, the operator releases the trigger mechanism 62 in the handle 60, corresponding to the handle illustrated in FIG. 7A, which withdraws the elongated member 30 into the lumen 38 of the sheath 36, thereby securing the stone 80 in the lumen 24 of the basket 10 between the proximal end 22 of the projection 20 and the proximal end 14 of the basket 10.

In one embodiment of the method according to the invention, the stone 80 may be fragmented by advancing lithotriptor 50 in the lumen 32 of the elongated member 30 and activating the lithotriptor 50, as illustrated in FIG. 8D. Kinetic energy of the moving lithotriptor 50 is transferred to the stone 80 upon impact of the distal end 52 of the lithotriptor 50 with stone 80, resulting in fragmentation of the stone 80 into one or more pieces 81, 83. The projection 20 within the basket 10 not only secures the stone 80 within the lumen 24 of the basket 10 during impact to prevent the stone 80 from escaping, but also acts as a stress concentrator on the stone 80 facilitating breakage of the stone 80. The lithotriptor 50 may be activated one or more times to continue to fragment the stone pieces 81 into smaller, fragments 82, which may then be removed from the patient's body. As the stone pieces 81 fragment into smaller fragments 82, the basket legs 12 are withdrawn further into the lumen 38 of the sheath 36 and further secure the fragments 82, as shown in FIG. 8E. In an alternative embodiment, a laser lithotriptor 50 may be used to fragment the stone 80.

After fragmentation of the stone 80 is complete, the spring 64, as illustrated in FIG. 7A, pulls the basket legs 12 further within the lumen 38 of the sheath 36, thereby placing the basket 10 in the collapsed position, as shown in FIG. 8F. The operator may then remove the device 5 from the patient's body.

Figure 9A:
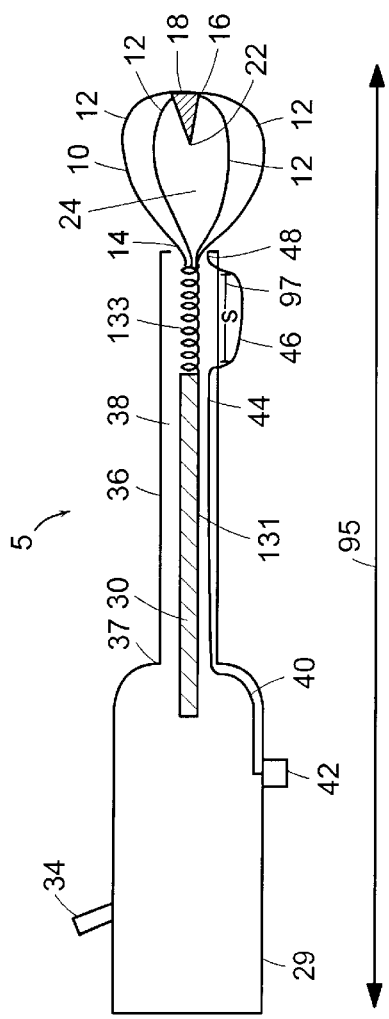
FIG. 9A is a plan view of another embodiment of the device of the invention including a basket, which can be tilted off axis by an operator.
Figure 9B:
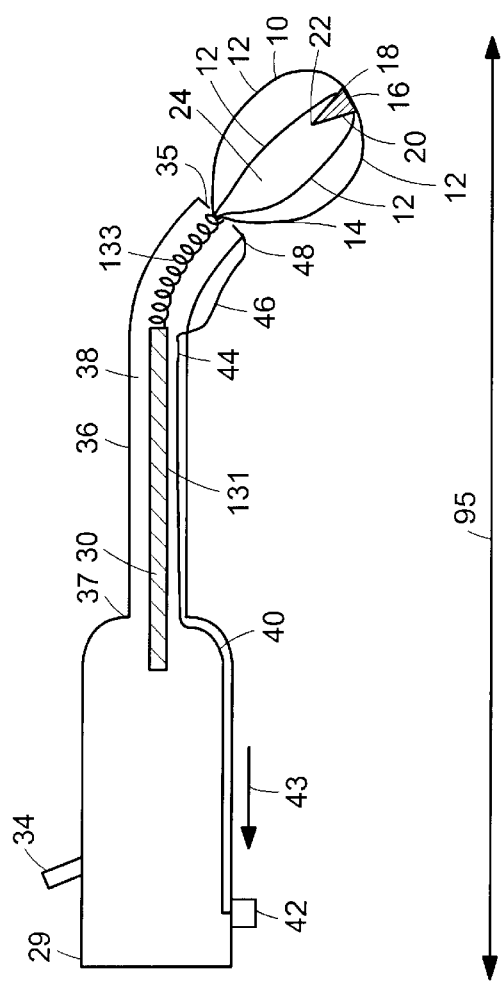
FIG. 9B is a plan view of the device according to FIG. 9A after the operator has tilted the basket of axis.

In another embodiment of the device 5, the basket 10 illustrated in FIGS. 9A and 9B can be reversibly tipped to facilitate capture of material 80. The operator controlling the device 5 can bend the distal end 35 of the sheath 36 by retracting a slider 42 on the handle 29 in the direction of the arrow 43. The slider 42 is joined to a wire 40 that extends from the slider 42 and is operatively joined to the distal end 35 of the sheath 36. The wire 40 has a distal portion 48, an intermediate portion 46, and a proximal portion 44. The distal portion 48 is attached to the distal end 35 of the sheath 36 and penetrates through the sheath wall 39 approximately one inch proximal to the distal end 35 of the sheath 36. The intermediate portion 46 of the wire 40 extends along an external surface 41, as shown in FIG. 4B, of the sheath wall 39 for a distance "s" 97 and then penetrates through the sheath wall 39 into the lumen 38 of the sheath 36. Distance "s" 97 is in the range of 5% to 20% of the length of the sheath 36, preferably 10%. The proximal portion 44 of the wire 40 continues from the intermediate portion 46, and extends 8 inches to 33 inches, preferably 12.5 inches axially along the lumen 38 of the sheath 36, into handle 60 and connects to the slider 42.

As shown in FIGS. 9A and 9B, in one embodiment according to the invention the elongated member 30 may further include a proximal portion 131 and a distal portion 133, which is flexible. The distal portion 133 of the elongated member 30 is made from an elastic material that returns to its original shape after the distal portion 133 is deflected from a longitudinal axis 95 of device 5. In one embodiment, the distal portion 133 shown in FIGS. 9A and 9B is a spring. In an alternative embodiment, the distal portion 133 may be made from a super-elastic material, such as, for example, a nickel-titanium alloy. The embodiment shown in FIGS. 9A and 9B may further include a lumen 32 extending within the elongated member 30 and a lithotripsy system located and operative within the lumen 32 of the elongated member 30.

An operator may use the device 5 according to the embodiment shown in FIGS. 9A and 9B to capture and retrieve material 80, such as, kidney stones 80, from a body tract of a patient. Prior to inserting the device 5 into the patient's body, the operator positions the actuation mechanism 34 to collapse the basket 10 within the lumen 38 of the sheath 36. Subsequent to collapse of the basket 10, the operator inserts the device 5 into an externally accessible tract, such as the urinary tract. The operator then advances the device 5, preferable under endoscopic guidance, until the basket 10 is positioned adjacent to the kidney stone 80. To capture the stone 80, the operator first expands the basket 10 and then maneuvers the basket 10 using the slider 42 to deflect the distal end 35 of the sheath 36 and the basket 10. Once the stone is within the lumen 24 of the basket 10, the operator partially retracts the basket legs 12 to ensnare the stone within the lumen 24 of the basket 10.

After the stone 80 has been captured and secured within the lumen 24 of the basket 10, the operator returns the elongated member 30 to a substantially straight configuration by advancing the slider 42 to return the slider 42 to its original position. If the stone 80 captured within the lumen 24 of the basket 10 is large, the operator may perform a lithotripsy procedure to fragment the stone 80 to facilitate removal of the stone 80 from the patient's body. After fragmentation of the stone 80, the operator may then collapse the basket 10 within the lumen 38 of the sheath 36 and remove the device 5 from the patient's body.

Although the present invention has been described with reference to preferred embodiments, workers skilled in the art will recognize that changes may be made in form and detail without departing from the spirit and scope of the invention.

What is claimed is:

1. A device for treating a stone in a body of a patient, comprising:
 a sheath comprising a sheath wall, a distal end, a proximal end, and a lumen;
 an expandable basket slidably receivable by the lumen of the sheath, the basket for treating the stone, the basket having a collapsed position where the basket is enclosed within the sheath, and an expanded position where the basket extends from the distal end of the sheath, the basket comprising a distal tip, a proximal end, a lumen, and a projection, wherein the projection acts as a stress concentrator for facilitating breakage of the stone, the projection being pyramidal in shape and comprising a distal end, a proximal end, and at least three sides, the distal end of the projection being joined to the distal tip of the basket, and the proximal end of the projection being free within the lumen of the basket.

2. The device according to claim 1 wherein the proximal end of the projection comprises at least one tip.

3. The device according to claim 2 wherein the at least one tip is sharp.

4. The device according to claim 1 further comprising an elongated member axially positioned in the lumen of the sheath, and operatively joined to the proximal end of the basket.

5. The device according to claim 4, wherein the elongated member further comprises a lumen axially positioned in the elongated member and in fluid communication with the basket lumen.

6. The device of claim 4 further comprising a basket handle positioned at the proximal end of the sheath and being operatively joined to the elongated member.

7. The device of claim 6 wherein the basket handle further comprises a spring operatively joined to the elongated member wherein the spring provides a predetermined force on the basket.

8. The device according to claim 1 further comprising a basket handle positioned at the proximal end of the sheath, the basket handle comprising a slider operatively joined to the proximal end of the sheath wherein the slider moves the sheath axially from a first position to a second position.

9. The device according to claim 1 wherein the distal end of the sheath is reinforced.

10. The device of claim 1 further comprising a wire for deflecting the sheath, the wire comprising a distal portion, an intermediate portion, and a proximal portion, the distal portion of the wire being attached to the distal end of the sheath.

11. The device according to claim 10 wherein said wire is axially positioned along an external surface of the sheath, the intermediate portion of the wire penetrating the sheath wall, and the proximal portion of the wire extending proximally within the lumen of the sheath.

12. The device according to claim 11 further comprising an elongated member axially positioned in the lumen of the sheath, and operatively joined to the proximal end of the basket.

13. The device according to claim 12 wherein the elongated member defines a lumen axially positioned in the elongated member and in fluid communication with the basket lumen.

14. The device according to claim 13 wherein the elongated member further comprises a distal portion and a proximal portion, wherein the distal portion comprises an elastic material.

15. The device according to claim 14 wherein the distal portion comprises a shape memory alloy.

16. The device according to claim 14 wherein the distal portion comprises a spring.

17. The device according to claim 1 wherein the proximal end of the projection comprises a plurality of tips.

18. The device according to claim 1, wherein the proximal end of the projection comprises a blunt tip.

19. The device according to claim 1, wherein the projection projects into the lumen of the basket in a range of about 1–35% of the length of the basket.

20. A method for fragmenting captured material in a body, comprising:
 inserting a device into the body of a patient, the device comprising a sheath comprising a sheath wall, a distal end, a proximal end, and a lumen, an expandable basket slidably receivable by the lumen of the sheath, the basket for treating material in a body, the basket having a collapsed position where the basket is enclosed within the sheath, and an expanded position where the basket extends from the distal end of the sheath, the basket comprising a distal tip, a proximal end, a lumen, and a projection, wherein the projection acts as a stress concentrator for facilitating breakage of material, the projection being pyramidal in shape and comprising a distal end, a proximal end, and at least three sides, the distal end of the projection being joined to the distal tip of the basket, and the proximal end of the projection being free within the lumen of the basket;
 placing the basket in the expanded position;
 maneuvering the basket to grasp the material;
 collapsing the basket to fragment the material; and
 withdrawing the device from the body.

* * * * *